(12) United States Patent
Weiner

(10) Patent No.: US 9,200,274 B2
(45) Date of Patent: Dec. 1, 2015

(54) EXPANDED RADIX FOR POLYMERIC TAGS

(71) Applicant: Michael P. Weiner, Guilford, CT (US)

(72) Inventor: Michael P. Weiner, Guilford, CT (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 14/359,558

(22) PCT Filed: Nov. 19, 2012

(86) PCT No.: PCT/US2012/065929
§ 371 (c)(1),
(2) Date: May 20, 2014

(87) PCT Pub. No.: WO2013/085710
PCT Pub. Date: Jun. 13, 2013

(65) Prior Publication Data
US 2014/0342921 A1    Nov. 20, 2014

Related U.S. Application Data

(60) Provisional application No. 61/569,027, filed on Dec. 9, 2011.

(51) Int. Cl.
| | | |
|---|---|---|
| C12N 15/10 | (2006.01) | |
| C12Q 1/68 | (2006.01) | C40B 20/00 |
| (2006.01) | | C40B 30/00 |
| (2006.01) | | |

(52) U.S. Cl.
CPC .......... *C12N 15/1065* (2013.01); *C12Q 1/6816* (2013.01); *C12Q 1/6874* (2013.01); *C40B 20/00* (2013.01); *C40B 30/00* (2013.01)

(58) Field of Classification Search
None
See application file for complete search history.

(56) References Cited

U.S. PATENT DOCUMENTS

| | | |
|---|---|---|
| 2003/0108900 A1 | 6/2003 | Oliphant et al. |
| 2006/0073506 A1 | 4/2006 | Christians et al. |

FOREIGN PATENT DOCUMENTS

| | | |
|---|---|---|
| WO | 2005/068656 | 7/2005 |
| WO | 2011/052586 | 5/2011 |

OTHER PUBLICATIONS

Tobler et al., "The SNPlex Genotyping System: A Flexible and Scalable Platform for SNP Genotyping," J. Biomol. Tech. 2005, 16:398-406.*

Weiner, Michael, "BarCoding DNA," PowerPoint Presentation, Sep. 14, 2011, pp. 1-17.

* cited by examiner

*Primary Examiner* — Samuel Woolwine
*Assistant Examiner* — Kaijiang Zhang
(74) *Attorney, Agent, or Firm* — John T. Murphy; Illumina, Inc.

(57) ABSTRACT

A method having steps of (a) providing nucleic acids having a tag sequence $(N_1)_n(N_2)_n \ldots (N_x)_n$, wherein $N_1$, $N_2$ and $N_x$ are nucleotides that complement different nucleotides, respectively, wherein n is an integer that can differ for $N_1$, $N_2$ and $N_x$; (b) detecting the nucleic acids individually and under conditions to distinguish signal intensities for $(N_1)_n$ sequences having different values for n, $(N_2)_n$ sequences having different values for n and. $(N_x)_n$ sequences having different values for n; and (c) distinguishing the tags based on the signal intensities.

13 Claims, 4 Drawing Sheets

A

B

EXPANDED RADIX FOR POLYMERIC TAGS

This application is based on, and claims the benefit of, U.S. Provisional Application No. 61/569,027, filed Dec. 9, 2011, and which is incorporated herein by reference.

This invention was made with government support under NIH grant number 1R43HG005282-01 awarded by the PHS. The United States Government has certain rights in this invention.

BACKGROUND

Nucleic acids are useful as tags for a variety of items. Nucleic acids can be used to tag large numbers of items because they provide a large repertoire of different 'words' that can be constructed from an alphabet of the four naturally occurring nucleotides: A, C, T (or U in the case of RNA) and G. Nucleic acids are appealing as tags because there are a variety of well established methods for accurately copying the words and deciphering the words. Thus nucleic acid tags can be archived, read multiple times, and amplified to increase copy number to suit various uses. Furthermore, nucleic acids are a relatively robust molecule that can be conveniently manipulated with an acceptably low risk of degradation.

However, as the number and length of the words in a nucleic acid tag increases, the techniques and systems required to decipher the tags become concomitantly more complex and expensive. What is needed are simplified ways to detect and decipher complex collections of nucleic acid tags. The present disclosure addresses this need and provides other advantages as well.

BRIEF SUMMARY

This disclosure provides a method having steps of (a) providing nucleic acids having a tag sequence $(N_1)_n(N_2)_n \ldots (N_x)_n$, wherein $N_1$, $N_2$ and $N_x$ are nucleotides that complement different nucleotides, respectively, wherein n is an integer that can differ for $N_1$, $N_2$ and $N_x$; (b) detecting the nucleic acids individually and under conditions to distinguish signal intensities for $(N_1)_n$ sequences having different values for n, $(N_2)_n$ sequences having different values for n and $(N_x)_n$ sequences having different values for n; and (c) distinguishing the tags based on the signal intensities. In particular embodiments a method of the present disclosure can include the steps of (a) providing a plurality of nucleic acid molecules, including individual nucleic acid types having a tag sequence, wherein the tag sequence includes the sequence $(N_1)_n(N_2)_n$, wherein $N_1$ and $N_2$ are nucleotides that complement different nucleotides, respectively, wherein n is a nonzero integer that can differ for $N_1$ and $N_2$, wherein the plurality of nucleic acid molecules have at least 10 of the tag sequences that are not the same; (b) detecting the individual nucleic acids under conditions to distinguish signal intensities for $(N_1)_n$ sequences having different values for n and to distinguish signal intensities for $(N_2)_n$ sequences having different values for n; and (c) distinguishing the nucleic acid tags based on the signal intensities detected in step (b).

Also provided herein is a tagging method that includes the steps of (a) providing a nucleic acid molecule having a tag with a known nucleotide sequence; (b) contacting the nucleic acid tag with a primer, a polymerase and a mixture of different nucleotide types under conditions to extend the primer by incorporation of different nucleotide types from the mixture to form an extended primer comprising a sequence that is complementary to at least a portion of the nucleic acid tag, wherein the mixture includes at least three different nucleotide types, each having a different base moiety, wherein one of the different nucleotide types includes a blocking moiety and at least two of the different nucleotide types are extension competent, and wherein the at least two nucleotide types that are extension competent have different labels, whereby the extended primer includes the different labels and the blocking moiety; (c) detecting the extended primer under conditions to distinguish the different labels; and (d) identifying the nucleic acid tag based on the detection of the different labels. The method can optionally include further steps of (e) removing the blocking moiety from the extended primer, thereby producing a deblocked extended primer, and (f) repeating steps (b) through (d) using the deblocked extended primer as the primer of step (b).

In one multiplex embodiment, this disclosure provides a method for distinguishing tags that includes the steps of (a) providing a plurality of nucleic acid molecules, wherein individual nucleic acid molecules in the plurality have a universal priming site and a tag having a unique nucleotide sequence: (b) contacting the plurality of nucleic acid molecules with universal primers, a polymerase and a mixture of different nucleotide types under conditions to extend the universal primers by incorporation of different nucleotide types from the mixture to form extended primers having sequences that are complementary to at least a portion of the nucleic acid tags, wherein the mixture includes at least three different nucleotide types, each having a different base moiety, wherein one of the different nucleotide types has a blocking moiety and at least two of the different nucleotide types are extension competent, and wherein the at least two nucleotide types that are extension competent have different labels, whereby the extended primers have at least two of the labels and the blocking moiety; (c) detecting the extended primers under conditions to distinguish the different labels in each of the extended primers and under conditions to distinguish different extended primers; and (d) distinguishing the nucleic acid tags based on the detection of the different labels. Optionally, the method can further include the steps of (e) removing the blocking moiety from each of the extended primers, thereby producing a deblocked extended primers, and (f) repeating steps (b) through (d) using the deblocked extended primers as the universal primers of step (b).

A further example of a multiplex format is a method of identifying tag sequences that includes the steps of (a) providing a plurality of nucleic acid molecules, wherein different nucleic acid molecules in the plurality comprise different tag sequences, wherein the different tag sequences include at least two different nucleotide types each having a different label: (b) detecting each of the nucleic acid molecules in the presence of the at least two different nucleotide types each having a different label; (c) distinguishing the amount of the two different labels or the ratio of the two different labels for the nucleic acid molecules; and (d) identifying the tag sequences based on the amount of the two different labels or the ratio of the two different labels.

DETAILED DESCRIPTION

Figure 1:
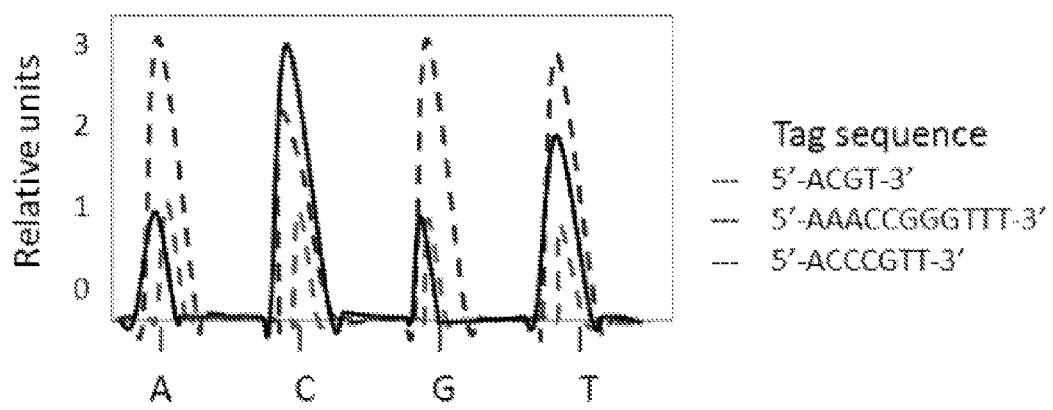
FIG. 1 shows a plot that distinguishes three different tag sequences based on the intensity of signals that would be produced from the tags in a sequencing system.

The present disclosure provides tags based on the sequence content of polymer molecules. By way of example, the tags will be described in the context of nucleic acid molecules such as DNA. However, as will be apparent from the examples, other polymer molecules can be used as well. Nucleic acid tags are typically based on a specific sequence of four nucleotides present in a nucleic acid polymer. As such, individual tags have been distinguished based on differences in the order of four different nucleotides in respective tags. Because nucleic acid tags typically have 4 distinguishable nucleotides, it can be thought of as providing a code system having a radix of 4. Accordingly, a population of nucleic acid tags of length N will have a code capacity (also referred to as a 'code space') of $4^N$ tags. The present disclosure provides an expansion of the code capacity of nucleic acid by expanding the numerical base of nucleic acid beyond a radix of 4. More generally, this disclosure provides for an expansion of the numerical base of a polymer code, such that the radix of the polymer code for a population of polymers is greater than the number of different monomers that are present in the polymers.

In one embodiment, the numerical base of a typical nucleic acid can be expanded by distinguishing multiple states for each of the four different nucleotides that are present in a population of nucleic acid polymers. For example, a population of tags can be constructed to provide 4 different nucleotides that are present in 3 different states (e.g. 1=low, 2=medium and 3=high). This would yield a radix of 81 and a code capacity of $81^N$ as shown by the example below:

$(A_1, A_2, A_3) (C_1, C_2, C_3) (G_1, G_2, G_3) (T_1, T_2, T_3)=(3\times3\times3\times3)=81^N$ The states of low, medium, and high can correlate, in one example, to the number of nucleotides of a particular type that are present in a region of a tag (e.g. a homopolymeric series). For example, low can be assigned to 1 nucleotide, medium can be assigned to 2 nucleotides and high can be assigned to 3 nucleotides. Other numbers of nucleotides in each region can be selected as desired to fit a particular format.

As exemplified above, the radix of nucleic acid codes can be expanded by detecting the number of nucleotides of a particular type that are present in a region (e.g. a homopolymeric series). Thus, in contrast to previous coding methods and tag systems, the present system does not require that the sequence of a tag be determined to single nucleotide precision. For example when using a set of DNA tags wherein the different nucleotide types are uniquely labeled, one need not read the sequences of the tags as a discrete set of digital signals such that the identity and location of each nucleotide is distinguished based on the labels. Rather, one can detect several labels simultaneously and distinguish different tags or codes based on differences in the intensity of the labels. Simultaneous detection in this way can provide for more rapid and cost effective detection compared to previous systems while providing an expanded code capacity. This is demonstrated by the example of sequencing-based detection systems where several nucleotide incorporation events can be detected in aggregate instead of the typical mode where incorporation of each nucleotide is detected individually and discretely.

The tags provided by the present disclosure can be detected using a variety of methods that are set forth in detail herein below. However, the tags are particularly well suited to sequencing-by-synthesis (SBS) methods. This can be illustrated briefly in regard to the above $base_{81}$ nucleic acid coding system that utilizes three states for four nucleotide types. FIG. 1 provides a simplified representation of SBS data that can be used to distinguish 3 tags. The data can be obtained using any of a variety of non-traditional SBS methods (e.g. modified versions of traditional methods or new methods altogether) as set forth in further detail herein below. As a result the three tags can have the same apparent sequence of nucleotides "ACGT" but the tags can differ in the apparent state for at least one of the nucleotides. As demonstrated in FIG. 1, the first tag would have an apparent sequence of ACGT and each nucleotide would be in an apparent state of 1. The second tag would have the same apparent sequence as the first tag, but the apparent states of the nucleotides would differ, being 3, 2, 3 and 3, respectively. The third tag would have the same apparent sequence as the first and second tag, but the apparent states would differ being 1, 3, 1 and 2, respectively.

Alternatively or additionally to expanding the number of codes by increasing the number of states, the code capacity can be increased by increasing the apparent length (N) of the tags. For example, the codes exemplified with regard to FIG. 1 have an apparent sequence of ACGT and an apparent length of 4 that can be expanded to an apparent length of 5 by adding a nucleotide other than T after the final T (i.e. ACGTA, ACGTC or ACGTG).

A useful option for increasing N, for example in SBS embodiments, is to utilize at least one nucleotide type that serves as a punctuation mark between code regions. A population of tags can be constructed to have several code regions where each code region has 3 different nucleotides that are present in 3 different states. This would yield a radix of 27 and a code capacity of $27^N$ for each code regions as shown by the example below:

$(A_1, A_2, A_3) (C_1, C_2, C_3) (G_1, G_2, G_3)=(3\times3\times3)=27^N$

The code regions can be separated by a T nucleotide to provide punctuation to the code and a means to partition the detection of each code region. For example, the codes can be detected in an SBS method wherein the three nucleotides A, C and G lack any blocking moiety, such that a polymerase can incorporate one or more nucleotides of all three types into a nascent strand (e.g. a primer) during a single extension step of a sequencing cycle. The three nucleotide types can also have a uniquely identifiable label such that the nucleotide types can be distinguished one from the other during a detection step. During the cycle a T nucleotide can also be delivered (e.g. during the same step that the A, C and G nucleotides are delivered or in a separate step of the cycle). The T nucleotide can optionally have a reversible blocking moiety such that once it is incorporated into the nascent strand, further extension is prevented (the T nucleotide may or may not have a detectable label). In one example, the T nucleotide serves as a punctuation mark due to being delivered to an SBS substrate in a separate flow from the flow(s) used to deliver other nucleotide types. As such, the T nucleotide need not have a reversible blocking moiety. In another example, the T nucleotide need not be delivered in a separate flow and serves as a punctuation mark due to the presence of a reversible blocking moiety.

The labels from several nucleotide types may be present during detection and as such the labels may be apparently detected in aggregate. However, nucleotides outside of the code region will not be detected since the punctuating T nucleotide temporarily pauses sequencing outside of the region (e.g. T may have a reversible blocking moiety or T may be delivered in a separate flow from other nucleotide types). A second region can however be accessed, for example by deblocking the T nucleotide or managing reagent flows, and the sequencing cycle can be repeated. A nucleotide that is used as a punctuation mark may have a label; however, a label need not be present on nor detected for a nucleotide that is used as a punctuation mark.

The tag in the above example is described with respect to the strand that is synthesized in the polymerase extension step. Those skilled in the art will understand that a nucleic acid tag can be readily recognized from either of two complementary strands. As such, description of a nucleic acid tag sequence herein is intended to encompass and describe its complement unless explicitly or contextually indicated to the contrary.

Various embodiments of the tags and methods set forth herein are, at least in some ways, analogous to a molecular restriction fragment length polymorphism (RFLP) technique. For example, the methods can be used for fingerprinting DNA using readily available SBS techniques. More specifically, the differences between two sequences (reading A, C, and G intensities relative to a T punctuation) would become apparent as the SBS reaction went into and then exited a polymorphic region of a target DNA. Methodology of the present disclosure can allow the changes to be identified 4 times faster when using embodiments where 4 different bases are simultaneously detected compared to the time required for a traditional SBS technique. This in turn allows much larger DNA fragments to be read, since the loss in registry (e.g. phasing and dephasing) that occurs at every cycle in many current commercial systems may occur much less frequently in a sequenced region when only one blocking nucleotide is used per 4 nucleotides. In cases where resequencing is being performed relative to a reference sequence, a fingerprint obtained by methods set forth herein can be helpful for determining the position of one or more sequence reads in the reference genome.

A more detailed understanding of the compositions and methods of the present disclosure can be gained from the following definitions and exemplary embodiments.

As used herein, the term "nucleotide" is intended to include natural nucleotides, analogs thereof, ribonucleotides, deoxyribonucleotides, dideoxyribonucleotides and other molecules known as nucleotides. The term can be used to refer to a monomer unit that is present in a polymer, for example to identify a subunit present in a DNA or RNA strand. The term can also be used to refer to a monomeric molecule that is not present in a polymer, for example, a molecule that is capable of being incorporated into a polynucleotide in a template dependent manner by a polymerase. A nucleotide can have a base moiety including, but not limited to, adenine (A), guanine (G), thymine (T), uracil (U), cytosine (C), inosine, xanthanine, hypoxanthanine, isocytosine, isoguanine, nitropyrrole (including 3-nitropyrrole) or nitroindole (including 5-nitroindole). Exemplary natural nucleotides include, without limitation, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP.

As used herein, the term "tag" means a polymer sequence having an identifiable characteristic. The polymer can be, for example, a nucleic acid. The identifiable characteristic can be, for example, the identity of one or more nucleotides in the sequence; the order of the nucleotides in the sequence, the position of one or more nucleotide types in the sequence, the number of nucleotides of one or more (e.g. 2, 3, 4 or more) particular types in the sequence, the ratio two or more nucleotides of a particular type in the sequence, a combination of two or more of the foregoing, or the absence of one or more of the foregoing. A nucleic acid sequence that is used as a tag may have identifiable characteristics that are not necessarily known or determined. For example, the number of nucleotides of one (or more) particular type can be known or determined without knowledge of the position of the nucleotides in the sequence or without knowledge of the order of nucleotides in the sequence. Other polymers that can form tags include, for example, polypeptides, polysaccharides, peptide nucleic acid and synthetic polymers.

As used herein the term "type," when used in reference to a monomer, nucleotide or other unit of a polymer, is intended to refer to the species of monomer, nucleotide or other unit. The type of monomer, nucleotide or other unit can be identified independent of their positions in the polymer. Similarly, when used in reference to a symbol or other identifier in a sequence, the term is intended to refer to the species of symbol or identifier and can be independent of their positions in the sequence. Exemplary types of nucleotides are those known in the art as adenine (A), cytosine (C), guanine (G), thymine (T), or uracil (U).

As used herein the term "position," when used in reference to a sequence of units, refers to the location of a unit in the sequence. The location can be identified using information that is independent of the type of unit that occupies the location. The location can be identified, for example, relative to other locations in the same sequence. Alternatively or additionally, the location can be identified with reference to another sequence or series. Although one or more characteristic of the unit may be known, any such characteristics need not be considered in identifying position.

As used herein, the term "mixture of different nucleotide types" means a combination of two or more different species of nucleotide monomers. The different nucleotide types are simultaneously together, for example, in a liquid, in a gas, in a gel, on a surface or as a combination thereof. An exemplary combination is a surface bound reaction component that is in contact with a solution phase component. A mixture can be distinguished from a chemical compound in that the two or more different things are not necessarily in fixed proportions, need not lose their individual characteristics, and can be separated by physical means. It will be understood that two or more different nucleotide types in a reaction can react with each other to subsequently form a nucleic acid.

As used herein, the term "extend," when used in reference to a primer or other nucleic acid, means to add at least one nucleotide or oligonucleotide to the primer or nucleic acid. The addition can occur at the 3' or 5' end of a primer. For example, one or more nucleotides can be added to the 3' end of a primer by a polymerase. In another example, an oligonucleotide can be ligated to the 5' end of a primer or to the 3' end of the primer, for example, by a ligase. A nucleic acid that is extended can also be referred to as a 'nascent strand' or a 'growing strand'.

As used herein, the term "blocking moiety," when used in reference to a nucleotide, means a part of the nucleotide that inhibits or prevents the nucleotide from forming a covalent linkage to a second nucleotide. For example, in the case of nucleotide analogs having a pentose moiety, a blocking moiety can prevent formation of a phosphodiester bond between the 3' oxygen of the nucleotide and the 5' phosphate of the second nucleotide. The blocking moiety can be part of a nucleotide that is a monomer unit present in a nucleic acid polymer or the blocking moiety can be a part of a monomeric nucleotide (e.g. a nucleotide triphosphate). The blocking moiety that is part of a nucleotide can be reversible, such that the blocking moiety can be modified to render the nucleotide extension competent. Particularly useful reversible blocking moieties are set forth below and in references incorporated herein as set forth below. In particular embodiments, a blocking moiety, such as a reversible blocking moiety, can be attached to the 3' position or 2' position of a pentose moiety of a nucleotide.

As used herein, the term "deblock" means to modify or remove a blocking moiety of a nucleotide to render the nucleotide extension competent. A "deblocking agent" is a catalyst, enzyme, reagent or other substance that is capable of modifying or removing a blocking moiety. Particularly useful deblocking reactions and deblocking reagents are set forth below and in references incorporated herein as set forth below.

As used herein, the term "extension competent," when used in reference to a first nucleotide, means capable of forming a covalent linkage to a second nucleotide. The first nucleotide can be a monomer present in a nucleic acid, for example, at the 3' end of the nucleic acid, or equivalent position on a nucleic acid analog. The first nucleotide can be extension competent with respect to a polymerase catalyzed or ligase catalyzed reaction.

As used herein, the term "homopolymeric region" means a contiguous sequence of at least 2 monomers that are the same type (e.g. 2 nucleotides having the same base moiety). The length of contiguous sequence can be, for example, at least 3, 4, 5, 6, 7, 8, 9, 10, 15, 20, 25, 30, 35, 40, 45, 50, 100, 200 monomers (e.g. nucleotides) or more. Alternatively or additionally the contiguous sequence may, in some embodiments, be no longer than 250, 200, 100, 50, 45, 40, 35, 30, 25, 20, 15, 10, 9, 8, 7, 6, 5, 4, 3 or 2 monomers (e.g. nucleotides).

As used herein, the term "universal priming site" means a region of nucleotide sequence that is common to two or more nucleic acid molecules, where the two or more nucleic acid molecules also have regions of sequence differences. A universal sequence that may be present in different members of a collection of nucleic acid molecules can allow the replication or amplification of multiple different sequences using a universal primer that is complementary to the universal sequence. Thus, "universal primers" are nucleic acid molecules having a common nucleotide sequence that hybridize specifically to the same universal priming site. It will be understood that the common nucleotide sequence in a population of universal primers can be all or a portion of the primers so long as the nucleotide sequence is of sufficient length to hybridize specifically under the conditions used.

As used herein, the term "array" refers to a population of different molecules that are attached to one or more solid-phase substrates such that the different molecules can be differentiated from each other according to their relative location. An array can include different molecules that are each located at a different addressable location on a solid-phase substrate. Alternatively, an array can include separate solid-phase substrates each bearing a different molecule, wherein the different probe molecules can be identified according to the locations of the solid-phase substrates on a surface to which the solid-phase substrates are attached or according to the locations of the solid-phase substrates in a liquid such as a fluid stream. The molecules of the array can be nucleic acids such as nucleic acid primers, nucleic acid probes or nucleic acid templates.

As used herein, the term "each," when used in reference to a collection of items, is intended to identify an individual item in the collection but does not necessarily refer to every item in the collection unless the context clearly dictates otherwise.

This disclosure provides a tagging method that includes the steps of (a) providing nucleic acids having a tag sequence $(N_1)_n(N_2)_n \ldots (N_x)_n$, wherein $N_1$, $N_2$ and $N_x$ are nucleotides that complement different nucleotides, respectively, wherein n is an integer that can differ for $N_1$, $N_2$ and $N_x$; (b) detecting the nucleic acids individually and under conditions to distinguish signal intensities for $(N_1)_n$ sequences having different values for n, $(N_2)_n$ sequences having different values for n and $(N_x)_n$ sequences having different values for n; and (c) distinguishing the tags based on the signal intensities.

A tagging method can include the steps of (a) providing a plurality of nucleic acid molecules, including individual nucleic acid types having a tag sequence, wherein the tag sequence includes the sequence $(N_1)_n(N_2)_n$, wherein $N_1$ and $N_2$ are nucleotides that complement different nucleotides, respectively, wherein n is a non-zero integer that can differ for $N_1$ and $N_2$, wherein the plurality of nucleic acid molecules have at least 10 of the tag sequences that are not the same; (b) detecting the individual nucleic acids under conditions to distinguish signal intensities for $(N_1)_n$ sequences having different values for n and to distinguish signal intensities for $(N_2)_n$ sequences having different values for n; and (c) distinguishing the nucleic acid tags based on the signal intensities detected in step (b).

In particular embodiments of the above method, the tag sequence includes the sequence $(N_1)_n(N_2)_n(N_3)_n$, wherein $N_1$, $N_2$, and $N_3$, are nucleotides that complement different nucleotides, respectively, wherein n is a non-zero integer that can differ for $N_1$, $N_2$, and $N_3$, and wherein step (b) includes detecting the individual nucleic acids under conditions to distinguish signal intensities for $(N_1)_n$ sequences having different values for n, to distinguish signal intensities for $(N_2)_n$ sequences having different values for n, and to distinguish signal intensities for $(N_3)_n$ sequences having different values for n.

Furthermore, the tag sequence can include the sequence $(N_1)_n(N_2)_n(N_3)_n(N_4)_n$, wherein $N_1$, $N_2$, $N_3$, and $N_4$ are nucleotides that complement different nucleotides, respectively, wherein n is a non-zero integer that can differ for $N_1$, $N_2$, $N_3$ and $N_4$, and wherein step (b) includes detecting the individual nucleic acids under conditions to distinguish signal intensities for $(N_1)_n$ sequences having different values for n, to distinguish signal intensities for $(N_2)_n$ sequences having different values for n, to distinguish signal intensities for $(N_3)_n$ sequences having different values for n, and to distinguish signal intensities for $(N_4)_n$ sequences having different values for n.

Examples have been provided above for tags having up to 4 different nucleotide types (i.e. x=4). This is done for purposes of explanation, for example, to set forth certain characteristics of the tags and aspects of making and using the tags. For purposes of brevity and clarity further examples, although contemplated are not explicitly set forth. Those skilled in the art will understand that the tags of the present disclosure can include more than 4 different nucleotide types, including for example, non-naturally occurring nucleotide types. Thus, x can be 2, 3, 4, 5, 6, 7, 8, 9 or more. Furthermore, the above description is intended to relate to polymers beyond nucleic acids and monomers beyond nucleotides.

The value for n in the various embodiments set forth above and elsewhere herein can be any desired value including, but not limited to at least 1, 2, 3, 4, 5, 6, 7, 8, 9, 10, 20, 30, 40, 50, 60, 70, 80, 90 or 100. Alternatively or additionally, including, but not limited to, at most, 100, 90, 80, 70, 60, 50, 40, 30, 20, 10, 9, 8, 7, 6, 5, 4, 3, 2 or 1. In some embodiments, the value for n can be 0. For example, one or more tags in a collection can have a region $(N_x)_n$ that is perceived as and/or expected to be a dark state. Thus, not all tags need have a non-zero integer for all regions of the tag. Instead one or more tags in a collection can have at least one region where n is 0.

The tag sequence for each of the individual nucleic acid types (or other polymers) in a population of nucleic acids (or other polymers) can, in some embodiments, be the same length. However, the tag sequences need not be the same length and, in many embodiments, tags of different lengths will be present in the population. This may be the case for embodiments that utilize an expanded radix that is based on different numbers of nucleotides (or other monomers) of a particular type corresponding to different states of the nucleotide (or other monomer). Taking as an example an embodiment utilizing three states for each nucleotide, the low state can correlate to 1 nucleotide, the medium state can correlate to 2 nucleotides and the high state can correlate to 3 nucleotides. It may be desired to have a larger distinction between the low, medium and high states in which case any two states can differ by a count of more than 1 nucleotide. Accordingly, two states can differ by at least 2, 3, 4, 5, 10, 15, 20 or more nucleotides.

In the above example, three states are described. It will be understood that the number of states for one or more nucleotide types used in a code can be fewer than three including for example, 2 states or even 1 state. If desired a larger number of states can be utilized including, for example, one or more nucleotide types present in at least 3 states, at least 4 states, at least 5 states, at least 10 states or more. Although several embodiments are exemplified herein for tags in which each nucleotide type is present in the same number of states, it will be understood that a particular nucleotide type can be assigned more or fewer states than another nucleotide type. Thus, different nucleotide types can be present in different numbers of states in a particular set of tags. Accordingly individual tags can be distinguished based on the number of nucleotides of a particular type that are present in the tag or in a region of the tag (e.g. in a homopolymeric region). A similar variety of states can be used for other types of monomers besides nucleotides.

As will be appreciated from the variety of tag sequences and states for the monomers present in the sequences, a plurality of polymer molecules (e.g. nucleic acid molecules) can include at least 10, 25, 48, 49, 50, 96, 97, 100, 500, $1 \times 10^3$, $1 \times 10^4$, $1 \times 10^5$, $1 \times 10^5$, $1 \times 10^6$, $1 \times 10^7$, $1 \times 10^8$, or more tag sequences. Alternatively or additionally, a plurality of polymer molecules (e.g. nucleic acid molecules) can include at most 10, 25, 50, 100, 500, $1 \times 10^3$, $1 \times 10^4$, $1 \times 10$, $1 \times 10$, $1 \times 10^6$, $1 \times 10^7$, or $1 \times 10^8$ tag sequences.

A tag sequence can be detected by any of a variety of techniques known in the art to be appropriate for the polymers encoded by the tags. In particular embodiments, different monomer types can be distinguished based on different detectable labels. A label can be intrinsic to a particular monomer (e.g. an endogenous label) or can be an exogenous label, for example, being associated with or attached to an individual monomer. In some embodiments, labels will produce a signal that is proportional to the amount of label present. Accordingly, the number of monomers of a particular type that are present in a tag can be distinguished by detecting the intensity of signal produced by the label(s). Thus, different tags can be distinguished based on signal intensities.

Under some detection conditions, several different tags will have the same apparent sequence of monomers (e.g. nucleotides) but will be distinguished according to the apparent differences in the intensities for one or more monomers (e.g. nucleotides) in that sequence. An example is provided by FIG. 1. Here, three different tag sequences are selected that would have the same apparent sequence of nucleotides "ACGT" if detected in a traditional sequencing method that utilized four nucleotides lacking blocking moieties that were delivered separately and sequentially in the order A, C, G then T. Examples of such sequencing systems are pyrosequencing (e.g. commercially available platform from 454 Life Sciences a subsidiary of Roche), sequencing using γ-phosphate-labeled nucleotides (e.g. commercially available platform from Pacific Biosciences) and sequencing using proton detection (e.g. commercially available platform from Ion Torrent subsidiary of Life Technologies). As shown, the first tag ("ACTG") would yield four signals (an A signal, C signal, G signal and T signal) each having a relative intensity of 1. The second tag ("AAACCGGGTTT") would yield the same sequence of four signals (A, C, G and T) as the first tag, but the relative intensities of the signals would differ (3, 2, 3 and 3, respectively) from the first tag. The third tag ("ACCCGTT") would yield the same sequence of four signals as the first and second tag, but the relative intensities of the signals would differ (1, 3, 1 and 2, respectively) from the first and second tags. The differences in apparent signal intensities for the same nucleotide type in the tags can be thought of as different states for the nucleotide type.

In the example of FIG. 1 and in several other examples set forth herein, the individual tag sequences in a population of tags have the same apparent order of nucleotide types (e.g. for a population of tags having the sequence $(N_1)_n(N_2)_n(N_3)_n(N_4)_n$, the $N_1$ nucleotide(s) is/are followed by the $N_2$ nucleotide(s) which is/are followed by the $N_3$ nucleotide(s) which is/are followed by the $N_4$ nucleotide(s) in each tag). However, in some embodiments, the apparent order of nucleotides need not be the same for all tags in a population. For example, different nucleotide types can be distinguished one from the other based on the type of label that is attached to the nucleotide. In this embodiment, the order of the nucleotides in each individual tag sequence need not be determined so long as the differences in the number of each nucleotide type can be distinguished for each individual tag. By distinguishing nucleotide types based on unique labels, a plot similar to that shown in FIG. 1 could be obtained no matter what the order of A's, C's, G's and T's were present in the three tags so long as the first tag had only one of each nucleotide; the second tag had three each of A, G and T and one of C and tag 3 had one each of A and G, three of C and two of T. The preceding applies to monomers other than nucleotides as well.

Optically detectable labels are particularly useful. Examples include chromophores, luminophores and fluorophores. Fluorophores are particularly useful and include, for example, fluorescent nanocrystals; quantum dots, fluorescein, rhodamine, tetramethylrhodamine, eosin, erythrosin, coumarin, methyl-coumarins, pyrene, Malacite green, Cy3, Cy5, stilbene, Lucifer Yellow, Cascade Blue, Texas Red, Alexa dyes, SETA dyes, Atto dyes, phycoerythin, bodipy, and analogs thereof. Useful optical probes are described in Haugland, *Molecular Probes Handbook*, (Eugene, Oreg.) 6th Edition; The Synthegen catalog (Houston, Tex.), Lakowicz, *Principles of Fluorescence Spectroscopy*, 2nd Ed., Plenum Press New York (1999), or WO 98/59066; WO 91/06678 or US Pat. Appl. Publ. No. 2010/0092957 A1, each of which is incorporated herein by reference in its entirety.

Other labels, some of which are non-optical labels, can be used in various embodiments of the methods and compositions set forth herein. Examples include, without limitation, an isotopic label such as a naturally non-abundant radioactive or heavy isotope; magnetic substance; electron-rich material such as a metal; electrochemiluminescent label such as Ru(bpy)$_3^{2+}$; or moiety that can be detected based on a nuclear magnetic, paramagnetic, electrical, charge to mass, or thermal characteristic. Labels can also include magnetic particles or optically encoded nanoparticles.

Another type of label that can be useful is a secondary label that is indirectly detected, for example, via interaction with a primary label, binding to a receptor, or conversion to a detectable product by an enzyme catalyst or other substance. An exemplary secondary label is a ligand such as biotin or analogs thereof that can be detected via binding to a receptor such as avidin, streptavidin or analogs thereof. Other useful ligands are epitopes that can bind to receptors such as antibodies or active fragments thereof, and carbohydrates that can bind to receptors such as lectins.

A label that is used in a method or composition set forth herein can be an intrinsic label (i.e. an endogenous label) that is present in a naturally occurring molecule being detected, such as a proton or pyrophosphate that is released from a nucleotide analog upon incorporation into an extended primer. Alternatively or additionally to detection of an intrinsic label, one can detect a label that is exogenous to a natural nucleotide analog. Thus, in some embodiments solely exogenous probes are detected such that endogenous probes are not detected, in other embodiments solely endogenous probes are detected such that exogenous probes are not detected and in some embodiments a combination of exogenous and endogenous probes are detected.

For embodiments that utilize nucleic acid-based tags, detection of a target nucleic acid having the tag can be based on the hybridization of a labeled nucleic acid probe to the target nucleic acid. The resulting hybrid species can be detected using a method appropriate to the particular label present on the probe. For example, fluorescence can be detected by methods known in the art and described for example in Lakowicz, *Principles of Fluorescence Spectroscopy*, 2nd Ed., Plenum Press New York (1999). Other detection techniques that can be used include, for example, mass spectrometry which can be used to distinguish molecules based on its mass; surface plasmon resonance which can be used to distinguish molecules based on binding to a surface immobilized receptor such as a complementary probe in the case of a nucleic acid target; absorbance spectroscopy which can be used to distinguish molecules based on the wavelength of energy absorbed; calorimetry which can be used to distinguish molecules based on changes in temperature of the environment due to binding to a probe molecule; electrical conductance or impedance which can be used to distinguish molecules based on changes in electrical properties or in the electrical properties of the environment, magnetic resonance which can be used to distinguish molecules based on presence of magnetic nuclei, or other known analytic spectroscopic or chromatographic techniques.

Detection of polymers can be carried out in a multiplex format such as in an array format. For example, nucleic acid molecules to be detected can be provided in an array of nucleic acids. Individual nucleic acids, and in particular their tag sequences, can be distinguished in an array based on their location in the array. A target nucleic acid having a tag sequence can be detected directly on the surface of an array. Alternatively, an assay can be performed in a multiplex reaction (e.g. in solution) and a product of the reaction can be detected on the surface of an array. Any one of several assays can be used including for example, one or more of those described in U.S. Patent Application Publication Nos. 2003/0108867 A1; 2003/0108900 A1; 2003/0170684 A1; 2003/0207295 A1; or 2005/0181394 A1, each of which is hereby incorporated by reference in its entirety. Arrays can be detected using methods known in the art as described generally in U.S. Pat. No. 7,329,860; U.S. Pat. App. Pub. Nos. 2010/0111768 A1, or 2011/0220775 A1; or U.S. Ser. Nos. 61/438,486 or 13/006,206, each of which is hereby incorporated by reference in its entirety. Arrays can also be made and used in accordance with embodiments set forth below in regard to emulsion PCR and bridge amplification.

Sequencing techniques are particularly useful for detection of nucleic acid-based tags. For example in embodiments that utilize a plurality of nucleic acid molecules that includes individual nucleic acid species having a tag sequence, wherein the tag sequence includes the sequence $(N_1)_n(N_2)_n$, detection can include the steps of (i) contacting the nucleic acid molecules with a primer and a polymerase, (ii) delivering nucleotide $N_1$, or the complement thereof, under conditions to extend the primer to form an extended primer including a sequence $(N_1)_n$ or the complement thereof, (iii) detecting the individual nucleic acids under conditions to distinguish signal intensities for $(N_1)_n$ sequences having different values for n, and (iv) sequentially repeating steps (ii) and (iii) for subsequent nucleotides $N_2$, $N_3$, or $N_4$, or complements thereof. This sequencing technique utilizes sequential delivery of different nucleotide types.

Sequential delivery of different nucleotide types is not necessary for all embodiments as will be apparent for the exemplary embodiments set forth below. Sequencing can be carried out using delivery techniques whereby two or more different nucleotide types are present together during a primer extension reaction. For example, detection can include the steps of (i) contacting nucleic acid molecules with a primer and a polymerase, (ii) delivering a mixture comprising nucleotide $N_1$ and nucleotide $N_2$, or the complements thereof, under conditions to extend the primer to form an extended primer comprising a sequence $(N_1)_n(N_2)_n$ or the complement thereof, and (iii) detecting the individual nucleic acids under conditions to distinguish signal intensities for $(N_1)_n(N_2)_n$ sequences having different values for n. More complex mixtures can be used, including for example, additions of a third nucleotide $N_3$, fourth nucleotide $N_4$ or more nucleotides. In particular embodiments, one of nucleotide $N_1$, nucleotide $N_2$, etc. or the complements thereof, can include a blocking moiety.

Any of a variety of sequencing techniques can be used. Some embodiments include sequencing-by-synthesis (SBS) techniques to determine the composition of a nucleic acid-based tag. SBS techniques generally involve the enzymatic extension of a nascent nucleic acid strand through the iterative addition of nucleotides against a template strand. In traditional methods of SBS, individual steps can be carried out under conditions wherein incorporation of a single nucleotide monomer into the nascent strand is distinguished. In one such format, each SBS step can utilize four different nucleotide types that all have a blocking moiety but that each have a distinguishable label. As such, the species of nucleotide that is added to a particular nascent strand can be distinguished based on detection of a signal unique to that species. In another format, each SBS step can utilize a single nucleotide that lacks any blocking moieties and the species of nucleotide that is added to the nascent strand can be distinguished based on the detection of a signal and knowledge of which nucleotide species was delivered in the step. Such traditional methods can be useful in some embodiments set forth herein. However in many embodiments, the addition of each individual nucleotide to the nascent strand need not be distinguished. Rather, several nucleotides of a single species or several nucleotides of several different types can be detected in a way that they are not individually distinguished. Exemplary embodiments of such methods are set forth in further detail below.

Sequencing methods that traditionally use nucleotide monomers lacking blocking moieties include, for example, pyrosequencing (e.g. commercially available platform from 454 Life Sciences a subsidiary of Roche), sequencing using γ-phosphate-labeled nucleotides (e.g. commercially available platform from Pacific Biosciences) and sequencing using proton detection (e.g. commercially available platform from Ion Torrent subsidiary of Life Technologies). In methods using nucleotide monomers lacking blocking moieties, the number of different nucleotides added to a nascent strand in each cycle can be dependent upon the template sequence and the mode of nucleotide delivery. These methods are well suited to the use of tag sequences that are distinguished according to different homopolymers lengths. As such, the readout of each step will produce a different intensity based on a difference in the number of nucleotides that are present in a homopolymeric region. The repertoire of tags can be expanded beyond the use of homopolymers by introducing a punctuating (e.g. a nucleotides having a blocking moiety or a nucleotide that is delivered in a separate flow as set forth in further detail elsewhere herein). In such cases, the reversibly blocked nucleotide or nucleotide that is delivered in a separate flow, can function as punctuation between regions of a code.

Some embodiments of the methods set forth above, as well as other embodiments described herein, include pyrosequencing techniques. Pyrosequencing detects the release of inorganic pyrophosphate ($PP_i$) as particular nucleotides are incorporated into the nascent strand (Ronaghi et al. (1996) *Analytical Biochemistry* 242(1), 84-9; Ronaghi (2001) *Genome Res.* 11(1), 3-11; Ronaghi et al. (1998) *Science* 281 (5375), 363; U.S. Pat. No. 6,210,891; 6,258,568 or 6,274, 320, the disclosures of which are incorporated herein by reference in their entireties). In pyrosequencing, released $PP_i$ can be detected by being immediately converted to adenosine triphosphate (ATP) by ATP sulfurylase, and the level of ATP generated is detected via luciferase-produced photons.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in U.S. Pat. App. Publ. Nos. 2009/0026082 A1; 2009/0127589 A1; 2010/0137143 A1; or 2010/0282617 A1, each of which is incorporated herein by reference in its entirety.

Some embodiments can utilize detection of nucleotide incorporations through fluorescence resonance energy transfer (FRET) interactions between a fluorophore-bearing polymerase and γ-phosphate-labeled nucleotides as described, for example, in U.S. Pat. No. 7,329,492 and U.S. Pat. No. 7,211, 414 (each of which is incorporated herein by reference in their entireties) or nucleotide incorporations can be detected with zero-mode waveguides as described, for example, in U.S. Pat. No. 7,315,019 (which is incorporated herein by reference in its entirety) and using fluorescent nucleotide analogs and engineered polymerases as described, for example, in U.S. Pat. No. 7,405,281 or U.S. Pat. App. Pub. No. 2008/0108082 (each of which is incorporated herein by reference in their entireties). In one example single molecule, real-time (SMRT) DNA sequencing technology provided by Pacific Biosciences Inc. can be utilized with the methods described herein. In some embodiments, a SMRT chip or the like may be utilized (U.S. Pat. Nos. 7,181,122, 7,302,146, or 7,313, 308, incorporated by reference in their entireties). A SMRT chip comprises a plurality of zero-mode waveguides (ZMW) each of which can detect an individual nucleic acid during a sequencing process.

Several sequencing methods traditionally use nucleotide monomers having blocking moieties. For example, cycle sequencing can be accomplished by stepwise addition of reversibly blocked nucleotides containing, for example, a cleavable or photobleachable dye label as described, for example, in U.S. Pat. Nos. 742,767; 7,414,1163 or 7,057,026, each of which is incorporated herein by reference in its entirety. Each cycle can include steps of nucleotide delivery, detection and deblocking. This approach has been commercialized by Solexa (now Illumina Inc.), and is also described in WO 91/06678 and WO 07/123,744 (filed in the United States patent and trademark Office as U.S. Ser. No. 12/295, 337), each of which is incorporated herein by reference in its entirety. The availability of fluorescently-labeled blocking moieties in which both the termination can be reversed and the fluorescent label cleaved facilitates efficient cyclic reversible termination (CRT) sequencing.

In accordance with the methods set forth herein, methods that typically use nucleotides having blocking moieties can be modified to use one or more different nucleotide types that do not have a blocking moiety. In particular embodiments, two or more nucleotide types that lack a blocking moiety can be present in a sequencing reagent or delivered to a template nucleic acid in a single step of a sequencing cycle and detected in each other's presence during the cycle. Alternatively, two or more nucleotide types that lack a blocking moiety can be delivered in separate steps and then detected under conditions that the different types are detected in each other's presence. Thus, as is the case with pyrosequencing, several nucleotides can be added to a primer in a template directed fashion without the need for an intermediate deblocking step. The nucleotide monomers can contain labels for detection, such as fluorescent labels, and can be used in methods and instruments similar to those commercialized by Solexa (now Illumina Inc.). Preferably in such embodiments, the labels do not substantially inhibit extension under SBS reaction conditions. However, the detection labels can be removable, for example, by cleavage or degradation. Removal of the labels after they have been detected in a particular cycle and prior to a subsequent cycle can provide the advantage of reducing background signal and crosstalk between cycles. Examples of useful labels and removal methods are set forth elsewhere herein.

An SBS method that has been modified to use one or more nucleotides that lack terminator moieties can further utilize a nucleotide that serves as a punctuation mark in a tag. Such punctuation can be achieved, for example, by managing the nucleotide content of reagents used in SBS flows (i.e. steps of an SBS cycle). More specifically, a punctuation nucleotide can be delivered in a separate flow from the flow(s) used to deliver other nucleotide types. Thus, the punctuating nucleotide caps a region of a tag and the relative location of the punctuation mark in the tag can be determined from knowledge of the flow schedule. In some embodiments, punctuation can be achieved with a nucleotide having a reversible blocking moiety. A blocked nucleotide, whether added in a mixture or in a separate flow, will prevent SBS extension, thereby capping a region of a tag to serve as a punctuation mark in the tag. Accordingly, methods that typically use nucleotides having blocking moieties can be modified to use only a subset of nucleotide types that lack a blocking moiety. For example, a single reversibly blocked nucleotide can function as punctuation between regions of a code when used along with nucleotide(s) that lack a blocking moiety.

For embodiments that use nucleotides having reversible blocking moieties, reversible terminators/cleavable fluorophores can include a fluorophore linked to the ribose moiety via a 3' ester linkage (Metzker, *Genome Res.* 15:1767-1776 (2005), which is incorporated herein by reference in its entirety). Other approaches have separated the terminator chemistry from the cleavage of the fluorescence label (Ruparel et al., *Proc Natl Acad Sci USA* 102: 5932-7 (2005), which is incorporated herein by reference in its entirety). Further examples of modified nucleotides having reversible blocking moieties and techniques for deblocking them are described in U.S. Pat. No. 7,427,673, or 7,057,026, the disclosures of which are incorporated herein by reference in their entireties. Additional examples of reagents, systems and methods which can be utilized in SBS embodiments are described in U.S. Pat. App. Pub. Nos. 2005/0100900 A1, 2007/0166705 A1, 2006/0188901 A1, 2006/0240439 A1, or 2006/0281109 A1; PCT Pub. Nos. WO 05/065814, WO 06/064199 or WO 07/010,251; or U.S. Pat. No. 7,057,026, the disclosures of which are incorporated herein by reference in their entireties.

Several other traditional sequencing methods and platforms can be modified to include the tags set forth herein as well as the methods for making and using the tags that are set forth herein. Some embodiments can utilize a version of SBS known as sequencing-by-ligation. Such techniques utilize DNA ligase to incorporate oligonucleotides and identify nucleotides in a template based on the incorporation of such oligonucleotides. Exemplary sequencing-by-ligation systems and methods which can be utilized with the methods and systems described herein are described in U.S. Pat. No. 6,969,488, U.S. Pat. No. 6,172,218, and U.S. Pat. No. 6,306,597, the disclosures of which are incorporated herein by reference in their entireties. Another useful sequencing technique is nanopore sequencing (see, for example, Deamer et al. *Trends Biotechnol.* 18, 147-151 (2000); Deamer et al. *Acc. Chem. Res.* 35:817-825 (2002); Li et al. *Nat. Mater.* 2:611-615 (2003), the disclosures of which are incorporated herein by reference in their entireties). In some nanopore embodiments, the target nucleic acid or individual nucleotides removed from a target nucleic acid pass through a nanopore. As the nucleic acid or nucleotide passes through the nanopore, each nucleotide type can be identified by measuring fluctuations in the electrical conductance of the pore. (U.S. Pat. No. 7,001,792; Soni et al. *Clin. Chem.* 53, 1996-2001 (2007); Healy, *Nanomed.* 2, 459-481 (2007); Cockrofl et al. *J. Am. Chem. Soc.* 130, 818-820 (2008), the disclosures of which are incorporated herein by reference in their entireties).

The sequencing methods described herein can be advantageously carried out in multiplex formats such that multiple different target nucleic acids are manipulated simultaneously. All or part of the sequence of each target nucleic acid can be a tag sequence. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically bound to a surface in a spatially distinguishable manner. The target nucleic acids can be bound by direct covalent attachment, attachment to a bead or other particle or binding to a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described below.

Various protocols can be used to generate an array of spatially immobilized nucleic acid features. For example, the features can be generated by emulsion PCR, or bridge amplification.

In embodiments using emulsion PCR, an in vitro-constructed adaptor flanked shotgun library can be PCR amplified in a water-in-oil emulsion. In particular embodiments the adapters can include a tag. Alternatively or additionally, a tag can be present in a target sequence. One of the PCR primers can be tethered to the surface (5'-attached) of micron-scale beads that are also included in the reaction. A low template concentration results in most bead-containing compartments having either zero or one template molecule present. In productive emulsion compartments (where both a bead and template molecule is present), PCR amplicons can be captured at the surface of the bead. After breaking the emulsion, beads bearing amplification products can be selectively enriched. Each clonally amplified bead will bear on its surface PCR products corresponding to amplification of a single molecule from the template library. Various embodiments of emulsion PCR methods that are useful are set forth in U.S. Pat. App. Publ. Nos. 2005/0042648 A1; 2005/0079510 A1 and 2005/0130173 A1, and WO 05/010145, each of which is incorporated herein by reference in its entirety.

In embodiments using bridge amplification, also known as cluster formation, an in vitro-constructed adaptor-flanked shotgun library can be PCR amplified using primers coated on the surface of a substrate. Again the adapters and/or target sequences can include tags. The primers can be attached at their 5' ends by a flexible linker. Amplification products originating from any given member of the template library remain locally tethered near the point of origin. At the conclusion of the amplification, each clonal cluster contains several copies of a single member of the template library. Various embodiments of bridge amplification methods that are useful, such as those that use a PCR-like mechanism, are set forth in U.S. Pat. App. Publ. No. 2007/0128624 A1, WO 07/010,251, U.S. Pat. No. 6,090,592 and U.S. Pat. No. 5,641,658, each of which is incorporated herein by reference in its entirety.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

Also provided herein is a tagging method that includes the steps of (a) providing a nucleic acid molecule having a tag with a known nucleotide sequence; (b) contacting the nucleic acid tag with a primer, a polymerase and a mixture of different nucleotide types under conditions to extend the primer by incorporation of different nucleotide types from the mixture to form an extended primer comprising a sequence that is complementary to at least a portion of the nucleic acid tag, wherein the mixture includes at least three different nucleotide types, each having a different base moiety, wherein one of the different nucleotide types includes a blocking moiety and at least two of the different nucleotide types are extension competent, and wherein the at least two nucleotide types that are extension competent have different labels, whereby the extended primer includes the different labels and the blocking moiety; (c) detecting the extended primer under conditions to distinguish the different labels; and (d) identifying the nucleic acid tag based on the detection of the different labels. The method can optionally include further steps of (e) removing the blocking moiety from the extended primer, thereby producing a deblocked extended primer, and (f) repeating steps (b) through (d) using the deblocked extended primer as the primer of step (b).

A nucleic acid tag that is detected using the method above can include a homopolymeric region that contains (or complements) one of the different nucleotide types that is extension competent. Optionally, the nucleic acid tag can include a second homopolymeric region that complements another of the different nucleotide types that is extension competent. It will be understood that a similar method can be carried out using greater than two different nucleotide types that are extension competent. In such embodiments, the nucleic acid tag can include further homopolymeric regions that complement the additional nucleotide types that are extension competent. Accordingly, an extended primer that is produced in the method can include a homopolymer of at least one of the different nucleotide types that are extension competent. For example, an extended primer can include at least one, two, three or more homopolymeric regions, wherein each region includes one of the different nucleotide types that are extension competent.

A nucleic acid tag that is detected using the method above can include one or more heteropolymeric regions that contains (or complements) one of the different nucleotide types that is extension competent. It will be understood that a nucleic acid tag can include both a homopolymeric and a heteropolymeric region that contains (or complements) one of the different nucleotide types that is extension competent. Indeed in some embodiments, a nucleic acid tag need not include a homopolymeric region that contains (or complements) one of the different nucleotide types that is extension competent. Accordingly, an extended primer that is produced in the method can include a plurality of nucleotides of at least one of the different nucleotide types that are extension competent, whether or not the plurality of nucleotides is in a homopolymeric or heteropolymeric region. Thus, an extended primer can include at least two, three or more different nucleotide types that are extension competent.

As exemplified by the embodiment above, a method of this disclosure can include a step of contacting a nucleic acid tag with a primer, a polymerase and a mixture of different nucleotide types under conditions to extend the primer by incorporation of different nucleotide types from the mixture to form an extended primer comprising a sequence that is complementary to at least a portion of the nucleic acid tag. This step can be carried out using a sequencing-by-synthesis (SBS) method such as those set forth previously herein.

Although a method is exemplified above for an embodiment in which the mixture includes at least three different nucleotide types, it will be understood that the mixture can optionally include at least four different nucleotide types, wherein each nucleotide type has a different base moiety. In this embodiment, at least two or three of the different nucleotide types in the mixture can be extension competent, and the extension competent nucleotides can have labels that are distinguishable from each other. Furthermore, at most one, two or three of the different nucleotide types in the mixture can include a blocking moiety.

A nucleotide that is used in a method set forth in this disclosure can include a blocking moiety and a label. For example, in the method set forth above wherein one of the different nucleotide types that is used as a punctuation mark for a region of a tag (for example, being present in a mixture and including a blocking moiety), the nucleotide type that is used as a punctuation mark can further have a label that is distinguished when detecting the extended primer. However, the label is optional and in other embodiments the nucleotide type that is used as a punctuation mark will not have a label that is detected or distinguished when detecting the extended primer.

Detection of an extended primer that includes at least two different nucleotide types having different labels can be carried out under conditions wherein the different labels are distinguished based on a greater signal intensity for at least one of the labels compared to the signal intensity for another of the labels. Furthermore, the nucleic acid tag can be identified from the relative intensity between signals from at least two of the labels.

Under the detection conditions used in a method set forth herein different labels can be distinguished in an extended primer by detecting a first label and a second label at different times. Thus, temporal differentiation can be used to distinguish two or more labels that are simultaneously present in an extended primer. Alternatively, the different labels that are present in an extended primer can be detected in the presence of each other (e.g. being detected simultaneously).

The methods set forth above can also be carried out in a multiplex format. The multiplex methods can be carried out in a variety of formats including, for example, in liquid format or in a solid phase format. Exemplary formats are set forth herein in the context of nucleic acid arrays and multiplex sequencing-by-synthesis methods. Other formats known in the art or apparent to one skilled in the art in view of the disclosure herein can also be used. Reagents, methods, techniques and the like described in the context of embodiments above can be applied as appropriate to multiplex embodiments. Similarly, the description below, although exemplified in regard to multiplex embodiments, is not necessarily intended to be limited to multiplex embodiments.

In one multiplex embodiment, this disclosure provides a method for distinguishing tags that includes the steps of (a) providing a plurality of nucleic acid molecules, wherein individual nucleic acid molecules in the plurality have a universal priming site and a tag having a unique nucleotide sequence; (b) contacting the plurality of nucleic acid molecules with universal primers, a polymerase and a mixture of different nucleotide types under conditions to extend the universal primers by incorporation of different nucleotide types from the mixture to form extended primers having sequences that are complementary to at least a portion of the nucleic acid tags, wherein the mixture includes at least three different nucleotide types, each having a different base moiety, wherein one of the different nucleotide types has a blocking moiety and at least two of the different nucleotide types are extension competent, and wherein the at least two nucleotide types that are extension competent have different labels, whereby the extended primers have at least two of the labels and the blocking moiety; (c) detecting the extended primers under conditions to distinguish the different labels in each of the extended primers and under conditions to distinguish different extended primers; and (d) distinguishing the nucleic acid tags based on the detection of the different labels. Optionally, the method can further include the steps of (e) removing the blocking moiety from each of the extended primers, thereby producing a deblocked extended primers, and (f) repeating steps (b) through (d) using the deblocked extended primers as the universal primers of step (b).

A further example of a multiplex format is a method of identifying tag sequences that includes the steps of (a) providing a plurality of nucleic acid molecules, wherein different nucleic acid molecules in the plurality comprise different tag sequences, wherein the different tag sequences include at least two different nucleotide types each having a different label; (b) detecting each of the nucleic acid molecules in the presence of the at least two different nucleotide types each having a different label; (c) distinguishing the amount of the two different labels or the ratio of the two different labels for the nucleic acid molecules; and (d) identifying the tag sequences based on the amount of the two different labels or the ratio of the two different labels.

Multiplex methods can be used to identify nucleic acids in a population. Accordingly, the method can further include a step of distinguishing the nucleic acid molecules based on the tag sequences identified in step (d). The nucleic acids that are tagged in this method or other methods set forth herein can be from a genome or transcriptome of a particular organism. In this case, the tag can be used to identify the genome or transcriptome from a particular individual among many genomes and/or trasnscriptomes that are present in a mixed sample (i.e. a sample having genomes and/or trasnscriptomes from several individuals). It will be understood that the nucleic acids in a sample can include all or part of the sequences that are present in a genome, transcriptome or other nucleic acid fraction of an organism.

Exemplary organisms from which nucleic acid samples can be derived and tagged include, without limitation, eukaryotic (unicellular or multicellular) organisms. Exemplary eukaryotic organisms include a mammal such as a rodent, mouse, rat, rabbit, guinea pig, ungulate, horse, sheep, pig, goat, cow, cat, dog, primate, human or non-human primate; a plant such as *Arabidopsis thaliana*, corn (*Zea mays*), sorghum, oat (*oryza sativa*), wheat, rice, canola, or soybean; an algae such as *Chlamvdomonas reinhardtii*; a nematode such as *Caenorhabditis elegans*; an insect such as *Drosophila melanogaster*, mosquito, fruit fly, honey bee or spider; a fish such as zebrafish (*Danio rerio*); a reptile: an amphibian such as a frog or *Xenopus laevis*; a *dictyostelium discoideum*; a fungi such as *pneumocystis carinii, Takifugu rubripes*, yeast, *Saccharamoyces cerevisiae* or *Schizosaccharomyces pombe*; or a *plasmodium falciparum*. A method of the invention can also be used to tag nucleic acids of organisms such as prokaryotes, examples of which include a bacterium, *Escherichia coli*, staphylococci or *mycoplasma pneumoniae*; an archae; a virus, examples of which include Hepatitis C virus or human immunodeficiency virus; or a viroid.

The compositions and methods set forth herein can also be used to tag or identify a subfraction of nucleic acids from a particular organism or other type of sample. For example, tags can be used to identify sequences derived from a particular chromosome; sequences derived from a particular manipulation of a nucleic acid sample, such as cleavage of DNA by a transposase or restriction enzyme; or sequences derived from an organisms after a particular treatment such as a transcriptome harvested after a cell has been treated by a particular drug or stimulus. The compositions and methods set forth herein can also be used to tag or identify a metagenomic sample. Thus, nucleic acids from a plurality of different organisms can share a tag sequence. For example, the microbiome of an organism's gut can be harvested and tagged. Similarly, a collection of organisms from an environmental sample or from a tissue (e.g. a tissue suspected of harboring several organisms that may optionally include a potential pathogen) can be tagged. Such tagged samples can be created and detected using methods set forth herein.

Various embodiments of the methods set forth herein, whether multiplex or not, can include a detection step wherein nucleic acid molecules are detected in the presence of at least two different nucleotide types each having a different label. Depending upon the particular application of the methods, detection can occur in the presence of at least three, four or more different nucleotide types each having a different label. As set forth previously herein, the labels can be extrinsic to the nucleotides or can be exogenous labels that are attached or associated with the nucleotides. Typically, the different labels can be distinguished from each other under the conditions used for detection. For example, the labels can be detected in separate channels or using separate detectors that are configured to selectively detect particular labels. This is the case for different fluorescent labels that can be distinguished due to emission in different regions of the spectrum. As such, different detection channels or different detectors can be optically configured to selectively detect emission in a desired region of the spectrum where a target fluorescent label is known to emit and/or to reject emission in regions of the spectrum where non-target fluorescent labels emit. In the case of fluorescent labels, further distinction of different labels can be achieved by selective excitation, whereby the excitation energy is tuned to a region of the spectrum where a particular fluorescent probe is known to be excited and where other fluorescent probes are not substantially excited. It will be understood that in some cases detection of a desired signal for a target label may be accompanied by a contaminating amount of detection of another signal from a non-target label. Such situations can be accommodated by the methods set forth herein. For example, detection conditions or detector configurations can be selected to provide for an amount of cross talk that is sufficiently small to allow one label to be distinguished in the presence of other labels.

Detection in the methods set forth herein can be carried out under conditions wherein the amount of a particular label is determined. In some cases, the detection method can provide a level of precision that distinguishes the exact number of nucleotides present in a tag sequence. However, quantitation at single nucleotide precision need not be achieved in all embodiments of the methods. Rather, two tag sequences can be distinguished or identified based on a relative difference in the amounts of a nucleotide of a particular type in a first tag sequence compared to the amount of the same nucleotide type in a second tag sequence. In some cases the amounts can differ by 1 nucleotide. For example, one A nucleotide in a first tag can be distinguished from two A nucleotides in a second tag. However, depending on the conditions used and sensitivity of the detection methods, the amounts can differ by greater than 1 nucleotide. Alternatively or additionally to distinguishing tags based on the amounts of a particular label or nucleotide type, detection can be carried out under conditions wherein the ratio of two different labels (or nucleotide types) in one tag is distinguished from the ratio of the same two labels (or nucleotide types) in a second tag.

It will be understood that the above examples are directed to pair-wise comparison of two nucleotide types for purposes of illustration. The methods can be similarly applied to embodiments where more than two labels are used. Accordingly, the conditions of detection can be selected to distinguish the amount of several different labels and/or ratio of those labels. Furthermore, the above can be applied to monomers other than nucleotides as well.

Figure 2:
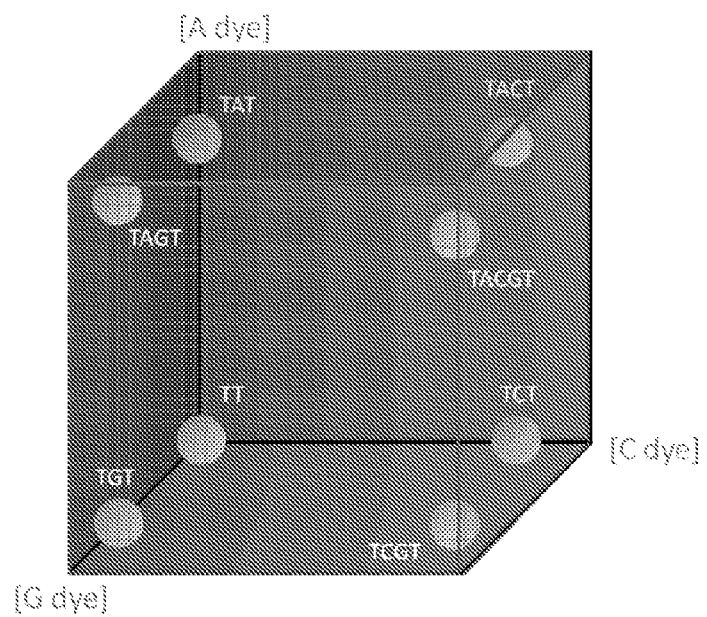
FIG. 2 shows representations for the code space available (a) when nucleotide order is not necessarily relied upon to distinguish codes and (b) when nucleotide order is used to distinguish codes.
Figure 2:
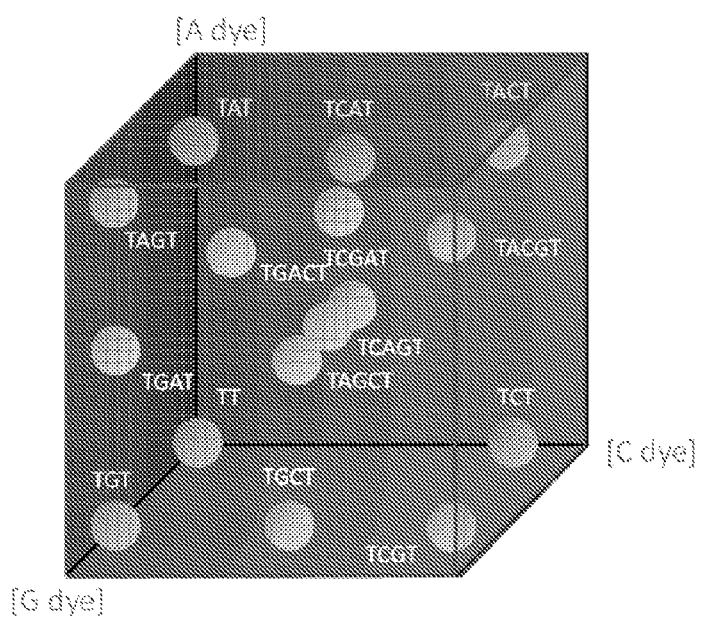

As demonstrated by the embodiments above, the sequence order for the different nucleotide types in a tag sequence need not be determined, at least not at single molecule resolution, in order to distinguish different tags in a method set forth herein. Rather, tags can be distinguished based on differences in the amount of two different labels (or nucleotide types) and/or the ratio of two different labels (or nucleotide types) that are present in the tags. FIG. 2 provides exemplary representations of the code space for collections of nucleic acid tags that are based on 3 labeled nucleotides. Panel A of the figure shows the code space provided by 8 exemplary codes that include 3 labeled nucleotides (A, C and G) along with a punctuating T nucleotide. The codes in panel A can be distinguished whether or not the order of nucleotides between the punctuating T nucleotides is determined. Panel B of the figure shows an expanded code space that results when the order of nucleotides is also determined. As demonstrated by FIG. 2, the order for the different nucleotide types in a tag sequence is not necessarily important for distinguishing the codes of the present disclosure. However, in some embodiments the order for the different nucleotide types in a tag sequences can be determined to increase the code space.

A particularly useful application of the tags of the present disclosure and related methods for detecting the tags is the decoding of random arrays of particles or beads. Beads or particles can be made that include a nucleic acid tag along with an analyte of interest. A population of such beads or particles can be randomly distributed in an array, for example, on the surface of the substrate or throughout a liquid array. The location of individual beads (and their respective analytes) in the array can be determined in a decoding process whereby the sequence of the respective nucleic acid tags is determined. Such arrays and methods for making the components of such arrays are described, for example, in U.S. Pat. Nos. 7,060,431; 7,033,754; or 7,226,734, each of which is incorporated herein by reference in its entirety. Arrays of random particles or beads, such as those described in these references, can be decoded using the nucleic acid tag sequences and detection methods set forth herein. A particular advantage of the current tags and decoding methods over other methods is the provision of a large number of tags (e.g. an increased radix and code space) that can be detected in a relatively low number of detection steps. For example, several embodiments described in U.S. Pat. Nos. 7,060,431; 7,033, 754; and 7,226,734 utilize multiple rounds of hybridization and detection to achieve a large code space. A benefit of the tags and detection methods of the current disclosure is that a similarly complex code space can be exploited in one or only a few steps of a sequencing reaction.

A further application of the tags of the present disclosure and related methods for detecting the tags is in multiplex nucleic acid assays. Such multiplex assays often utilize a tag to identify a locus, allele or other target nucleic acid sequence that is in a biological sample or believed to be in the sample. Exemplary multiplex assays that use tags include, but are not limited to, ligation assays (e.g. oligo ligation assay, circular probe ligation or padlock probe ligation), extension assays (e.g. single base extension and allele specific primer extension), extension-ligation assays, multiplex polymerase chain reaction assays, invasive cleavage, and cycling probe techniques. These and other assays are described in further detail, for example, in U.S. Pat. No. 6,355,431; 6,890,741; 6,913, 884; 7,955,794; 7,582,420 or 7,611,869 or U.S. Pat. App. Pub. Nos. 2002/0177141 A1 or 2003/0215821 A1, each of which is incorporated herein by reference in its entirety. Other examples of multiplex assays that use tags are the Golden-Gate Assay (commercially available from Illumina, Inc., San Diego Calif.), Padlock probe assay (developed by Parallele, commercially available from Affymetrix, Santa Clara, Calif.) and OLA (commercially available from O-Link, Sweden). In the aforementioned assays one or more of the probes can include a tag of the present disclosure and the tags can be detected using methods set forth herein.

EXAMPLE I

Expanding the Radix of Nucleic Acid Probes

The Arabic numeral system is an example of a place value notation based on the number 10 (i.e., $base_{10}$) and uses the digits 0 through 9. The concept of 'zero' has existed in the Arabic numeral system for approximately 1500 years. DNA can be thought of as having a place value notation of 4 (i.e. $base_4$) and uses the digits A, C, G, T. The concept of zero is not usually applied to DNA in most DNA encoding strategies.

This example describes a method for extending the utility of DNA encoding by expanding the numerical base of DNA beyond a radix of 4. In a described extreme example, the method will allow the ability to sequence 1 million single nucleotide polymorphisms (SNPs) in two to three sequencing cycles of sequencing-by-synthesis method, by encoding and using a tag sequence as a surrogate for the SNP. Such that by decoding the tag sequence, one would also know the SNP.

For converting a sequence from base 4 to base 10, the following formula can be used:

$$\sum_{i=0}^{n}(a_i \times b^i)$$

where i=exponentiation of the base, b. For example, the number 2303 in base $10=[(2\times10^3)+(3\times10^2)+(0\times10^1)+(3\times10^0)]$. But in base 4, the same number 2303 converted to base $10=[(2\times4^3)+(3\times4^2)+(0\times4^1)+(3\times4^0)]=[(2\times64)+(3\times16)+(0\times4)+(3\times1)]=128+48+0+3=179$.

Case 1, $base_4$ (standard) encoding: Assume 4 reversibly-terminating, separately distinguishable dye-labeled deoxynucleotides. Each flow of all four dye-terminators in a sequencing-by-synthesis reaction, together, provides a coding capacity of $4^N$ where N=number of cycles used.

Case 1, example 1: A flow of 5 cycles, where each cycle consists of: (a) polymerase extension, (b) dye-read, (c) terminator-reversal, would yield $4^5$ (=1024) possible codes.

Case 1, example 2 (A $1,024^{th}$ code of DNA sequence: TTTTT). In $base_4$ where A=0, C=1, G=2 and T=3, then TTTTT could be represented in $base_4$ as $33333_4$. Converting $base_4$ to $base_{10}$, $33333_4$ becomes $(3\times4^4)+(3\times4^3)+(3\times4^2)+(3\times4^1)+(3\times4^0)=(3\times256)+(3\times64)+(3\times16)+(3\times4)+(3\times1)=768+192+48+12+3=1,023$.

Case 1, example 3 (A Code of DNA sequence: ACGTC). In $base_4$ where A=0, C=1, G=2 and T=3, then ACGTC would be represented as $01231_4$. In $base_{10}$, $01231_4$ becomes $(0\times256)+(\times64)+(2\times16)+(3\times4)+(1\times1)=0+64+32+12+1=109$.

Case 2, $base_4$ encoding: Given 3 of the 4 possible natural nucleotides (for example A, C, G) used as separately-distinguishable and reversibly-labeled (nota bene, these nucleotides do not have a terminator moiety) dNTPs and a fourth labeled-nucleotide (T) that has a reversible-terminator moiety (serving as a 'punctuation mark'). Then each cycle of all four nucleotides together where the T nucleotide is incorporated last in a given coding sequence yields a coding capacity of $(2\times2\times2)^N=8^N$ where N=number of cycles used. The reason that it is 2×2×2 is that each cycle measures the presence or absence (0 or 1) of that nucleotide in that single cycle. In this example, the code sequence between the punctuation marks T is binary for the nucleotides A, C and G.

In the following examples, the following possible binary value combinations and their associated $base_8$ values are arbitrarily made: no A, C, or G bases (=0), A (=1), C (=2), G (=3), AC (=4), AG (=5), CG (=6), ACG (=7).

Case 2, example 1: A flow of 5 cycles would yield $8^5$ (=32,768) possible codes.

Case 2, example 2 (A $32,767^{th}$ code of DNA sequence): TACGTACGTACGTACGTACGT could be translated into the $base_8$ number $77777_8$, which can be converted into the base$_{10}$ number: $(7\times8^0)+(7\times8^1)+(7\times8^2)+(7\times8^3)+(7\times8^4)=(7\times1)+(7\times8)+(7\times64)+(7\times512)+(7\times4,096)=7+56+448+3,584+28,672=32,767$.

Case 2, example 3: A code of DNA sequence: ACG-TAGTCGTTACGT could be translated into the base$_8$ number 75607$_8$, which can be converted into the base$_{10}$ number $(7\times8^0)+(0\times8^1)+(6\times8^2)+(5\times8^3)+(7\times8^4)=(7\times1)+(0\times8)+(6\times64)+(5\times512)+(7\times4,096)=7+0+384+2,560+28,672=31,623$.

Case 3, base$_{27}$ encoding: This case utilizes grey-scale analysis whereby the intensity ('states') of a dye-label are determined during the code analysis. For example, a distinction can be detected between no incorporation of a dye ('low' state), the incorporation of a single dye-label ('medium' state), and the incorporation of two or more dye labels ('high' state). If 3 of the 4 possible nucleotides (for example A, C, G) are used as separately-distinguishable, reversibly-labeled dNTPs and a fourth labeled-nucleotide (T) is used as a reversible deoxynucleotide terminator ('punctuation mark') then each cycle of all four together, where the T nucleotide is incorporated at the 3' end of the code region sequence, yields a coding capacity of $(3\times3\times3)^N=27^N$ where N=number of sequencing cycles used. The reason that it is 3×3×3 is that for each cycle, the presence or absence of three dye-intensities (states) of low, medium or high are measured. In base$_{27}$, a flow of 5 cycles would yield $27^5$ (=14,348,907) possible codes.

Case 3, example 1 (A 14,348,90$^{th}$ code of DNA sequence): In this example, the following possible ternary value combinations and their associated base$_{27}$ values are made arbitrarily: no bases (A low, C low, G low=0), A (A medium, C low, G low=1), AA (A high, C low, G low=2), AC (A medium, C medium, G low=3), . . . AACCGG (A high, C high, G high=26).

TAACCGGTAACCGGTAACCGGTAACCGG-TAACCGGT could be translated into a base$_{27}$ number ZZZZZ$_{27}$ (where Z=26), which can be converted into the base$_{10}$ number $(26\times27^0)+(26\times27^1)+(26\times27^2)+(26\times27^3)+(26\times27^4)=(26\times1)+(26\times27)+(26\times729)+(26\times19,683)+(26\times531,441)=26+702+18,954+531,441+13,817,466=14,348,907$.

Case 4, base$_{1024}$ encoding: By way of extension of the code expansion cases above, assume the use of two non-native nucleotide base-pairs (a B1 pair and a second, B2 pair, for example d5SICS) to extend the genetic code. And furthermore, assume that four intensity levels can be distinguished (for example zero, one, two and four base homopolymers or heteropolymers). Each sequencing cycle is now composed of: (T punctuation) (4 intensity states of A) (4 intensity states of C) (4 intensity states of G) (4 intensity states of B1) (4 intensity states of B2) (T punctuation)=4×4×4×4×4=1024 different states per cycle. Two cycles using this scheme is $1024^2=1,048,576$. Five cycles using this scheme is $1024^5=1.13\times10^{15}$.

The number of codes can be expanded using 6 different dye labels and accordingly 6 excitation lines in a sequencing instrument. The number of lasers may not need to be increased for devices and systems that currently accommodate four dyes. Rather, dyes having similar emission spectra, but that change due to biochemical or biophysical properties can be used. Ideally, one dye would remain blank under one of these changed properties. For example, a system of method can be modified to use two dyes with similar spectra, for detection, but different spectra due to biochemical changes in pH, heat, salt concentrations, susceptible cleavage due to chemical agent (whereby subtraction is used to estimate the concentration of each dye) etc. In addition, changes due to fluorescence resonance energy transfer, heat or other properties can be exploited.

EXAMPLE II

Genotyping by Sequencing

Figure 3:
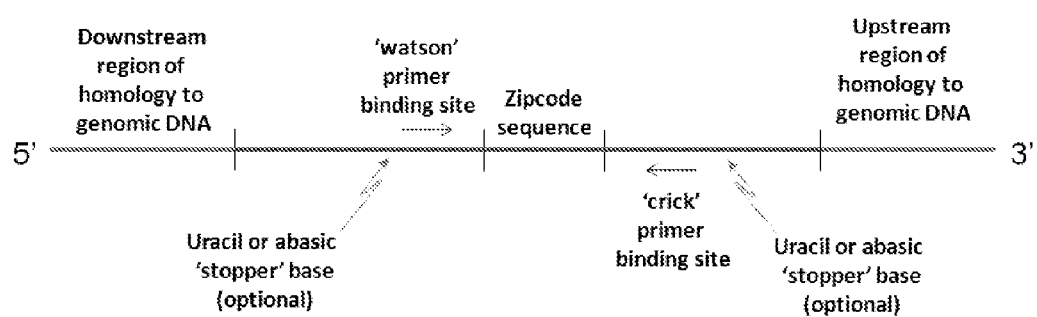
FIG. 3 shows an exemplary padlock probe.

A padlock probe can be designed to have the configuration shown in FIG. 3. As shown the probe includes (from 5' to 3') a downstream region with homology to a genomic DNA locus, a first optional uracil (or other locus that can be specifically cleaved), a first primer binding site (i.e. the 'Watson' priming site), a tag sequence (i.e. the "ZipCode sequence"), a second primer binding site (i.e. the 'Crick' priming site), a second optional uracil (or other locus that can be specifically cleaved), and an upstream region with homology to the genomic DNA locus.

The ZipCode sequence in the middle of the probe is a unique identifier (or surrogate sequence) for a SNP allele being queried at the genomic locus. The ZipCode, can be determined to identify the SNP that is queried by the probe. The 'Watson' and 'Crick' sequences can be complementary to the primers used to amplify fragments in a sequencing system. For example, bridge amplification primers used in an Illumina (Sand Diego, Calif.) platform or emulsion PCR primers used in a 454 Life Sciences (a subsidiary of Roche) or Ion Torrent (a subsidiary of Life Technologies) platform. The uracil or abasic sites represent places where a polymerase would stop during polymerization, or where the ZipCode can be cleaved from the probe using dut,ung enzymes. Additional methods for this purpose are also available, such as site-specific endonucleases. In a multiplex format, the Watson and Crick priming sites can be universal priming sites. Thus, each probe can have the same priming sites, but different ZipCodes and different locus specific regions (i.e. the ends that are homologous to genomic DNA).

Figure 4:
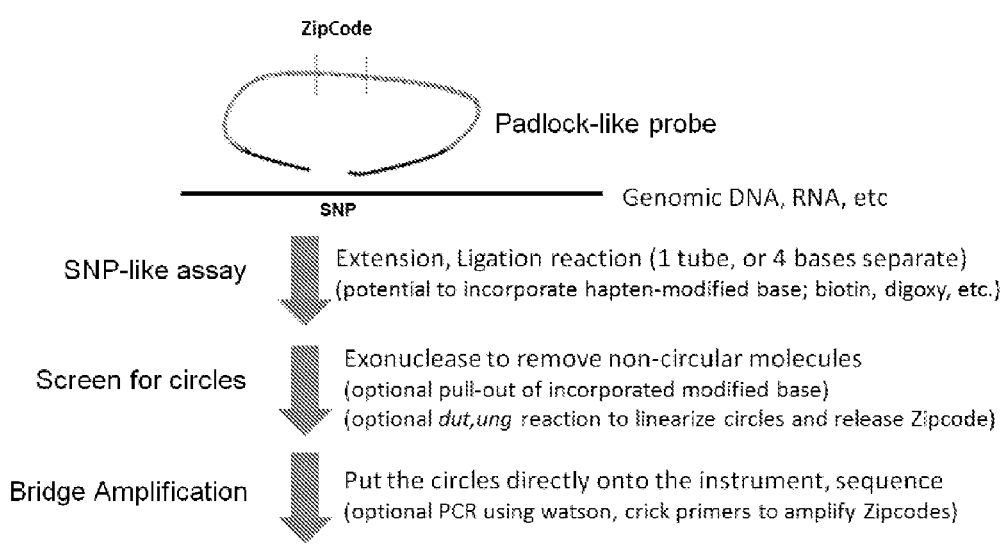
FIG. 4 shows a diagrammatic representation of an assay using padlock probes.

An example assay using the above padlock probe is shown in FIG. 4. The assay steps can be carried out as described in Hardenbol et al. *Nat. Biotech.* 21:673-678 (2003), except that the tags and the decoding methods can occur as set forth below and elsewhere in this disclosure. Depending on the format of the ZipCode, the decoding could occur in 2-5 cycles.

Given a known gene, it would be possible to design enough probes to 'ratchet' down an entire gene one base at a time, including all known polymorphisms. Enough codes are available. Using the base$_{27}$ scheme as a non-limiting example, this would allow an entire gene to be sequences in 2-4 cycles. By logical extension, an entire genome (bacterial, viral, human) could be sequences in just 2-3 cycles using probes having base$_{1024}$ tags.

The described ZipCoding strategy can be used to perform digital PCR counting (for example, as used in RNA-Seq techniques). Individual cDNAs can be labeled with a unique ZipCode. An array of 5 million probes can be used as complement to the ZipCodes. If (the number of cDNAs being counted)<(number of array features), then the presence or absence of a cDNA on an array feature can be tabulated.

In the above decoding methods and others set forth in this disclosure, an additional cycle can be used as a checksum to ensure the accuracy of the ZipCode decoding.

In the above decoding methods and others set forth in this disclosure, the extended bases can be null and hapten-labeled (biotin, digoxigenin, dintrophenol, S-methyl C, etc.) to allow, post incorporation, via immunoprecipitation, the ability to isolate extended, circularized molecules (or other probes). This allows the probe to be decoded and provides a means to verify which base was incorporated.

Copy number variation can be determined using the above probes by a comparison of the number of sequencing reads per specific base-site on the genome. Additional means can be used for analysis of insertions and deletions.

The methods above can be used to sequence viral, bacterial and other genomes by either designing 4 primers per base in the genome, or using hapten-labeled nucleotides. In addition to SNP and genomic sequencing, the encoding strategy can be used to separately label individual cDNA molecules and use such individually-labeled cDNAs for digital counting on an array.

Complement sequences on arrays, such as commercially available arrays, can be used as cZipCodes so that a single 5 million feature array can function as a platform to read any 5 million bases in a genome. Thus an array can be used as a universal array that is useful for any of a variety of species or analyses.

Throughout this application various publications, patents and patent applications have been referenced. The disclosures of these publications in their entireties are hereby incorporated by reference in this application.

The term "comprising" is intended herein to be open-ended, including not only the recited elements, but further encompassing any additional elements.

A number of embodiments have been described. Nevertheless, it will be understood that various modifications may be made. Accordingly, other embodiments are within the scope of the following claims.

What is claimed is:

1. A method, comprising
(a) providing a plurality of nucleic acid molecules, comprising individual nucleic acid types having a tag sequence,
wherein the tag sequence comprises the sequence $(N1)_n(N2)_m$,
wherein N1 and N2 are nucleotides that complement different nucleotides, respectively,
wherein n is a non-zero integer that can differ for N1 and N2,
wherein the plurality of nucleic acid molecules comprises at least 48 of the tag sequences that are not the same;
(b) detecting the individual nucleic acids under conditions to distinguish signal intensities for $(N1)_n$ sequences having different values for n and to distinguish signal intensities for $(N2)_n$ sequences having different values for n, wherein the detecting comprises:
(i) contacting the nucleic acid molecules with a primer and a polymerase,
(ii) delivering a mixture comprising nucleotide N1 and nucleotide N2, or the complements thereof, under conditions to extend the primer to form an extended primer comprising a sequence $(N1)_n(N2)_n$ or the complement thereof, and
(iii) detecting the individual nucleic acids under conditions to distinguish signal intensities for $(N1)_n(N2)_n$ sequences having different values for n; and
(c) distinguishing the nucleic acid tags based on the signal intensities detected in step (b).

2. The method of claim 1, wherein the tag sequence comprises the sequence $(N1)_n(N2)_n(N3)_n$,
wherein N1, N2, and N3, are nucleotides that complement different nucleotides, respectively,
wherein n is a non-zero integer that can differ for N1, N2, and N3, and
wherein step (b) comprises detecting the individual nucleic acids under conditions to distinguish signal intensities for $(N1)_n$ sequences having different values for n, to distinguish signal intensities for $(N2)_n$ sequences having different values for n, and to distinguish signal intensities for $(N3)_n$ sequences having different values for n.

3. The method of claim 2, wherein (ii) comprises delivering a mixture comprising nucleotide N1, nucleotide N2 and nucleotide N3, or the complements thereof, under conditions to extend the primer to form an extended primer comprising a sequence $(N1)_n(N2)_n(N3)_n$ or the complement thereof, and (iii) comprises detecting the individual nucleic acids under conditions to distinguish signal intensities for $(N1)_n(N2)_n(N3)_n$ sequences having different values for n.

4. The method of claim 3, wherein one of nucleotide N1, nucleotide N2 or nucleotide N3, or the complements thereof comprises a blocking moiety.

5. The method of claim 1, wherein the tag sequence comprises the sequence $(N1)_n(N2)_n(N3)_n(N4)_n$,
wherein N1, N2, N3, and N4 are nucleotides that complement different nucleotides, respectively,
wherein n is a non-zero integer that can differ for N1, N2, N3 and N4, and
wherein step (b) comprises detecting the individual nucleic acids under conditions to distinguish signal intensities for $(N1)_n$ sequences having different values for n, to distinguish signal intensities for $(N2)_n$ sequences having different values for n, to distinguish signal intensities for $(N3)_n$ sequences having different values for n, and to distinguish signal intensities for $(N4)_n$ sequences having different values for n.

6. The method of claim 5, wherein (ii) comprises delivering a mixture comprising nucleotide N1, nucleotide N2, nucleotide N3 and nucleotide N4, or the complements thereof, under conditions to extend the primer to form an extended primer comprising a sequence $(N1)_n(N2)_n(N3)_n(N4)_n$ or the complement thereof, and (iii) comprises detecting the individual nucleic acids under conditions to distinguish signal intensities for $(N1)_n(N2)_n(N3)_n(N4)_n$ sequences having different values for n.

7. The method of claim 6, wherein one of nucleotide N1, nucleotide N2, nucleotide N3 and nucleotide N4, or the complements thereof comprises a blocking moiety.

8. The method of claim 1, wherein n is an integer from 1 to 10.

9. The method of claim 1, wherein the tag sequence for each of the individual nucleic acid types in the plurality has the same length.

10. The method of claim 1, wherein the plurality of nucleic acid molecules comprises at least 96 of the tag sequences that are not the same.

11. The method of claim 1, wherein the plurality of nucleic acid molecules is provided in an array of nucleic acids.

12. The method of claim 1, wherein the individual nucleic acids are detected in an array.

13. The method of claim 1, wherein one of nucleotide N1 or nucleotide N2, or the complements thereof, comprises a blocking moiety.

* * * * *